United States Patent
Hubscher et al.

(10) Patent No.: US 6,824,975 B2
(45) Date of Patent: Nov. 30, 2004

(54) INCORPORATION OF SELECTIVE BINDING SUBSTANCES IN A SOLID PHASE ASSAY DEVICE

(75) Inventors: Thomas T. Hubscher, Gaithersburg, MD (US); Glen M Ford, Gaithersburg, MD (US); Teri M Ruppenthal, Hedgesville, WV (US)

(73) Assignee: Dexall Biomedical Labs, Inc, Gaithersburg, MD (US)

(*) Notice: Subject to any disclaimer, the term of this patent is extended or adjusted under 35 U.S.C. 154(b) by 134 days.

(21) Appl. No.: 09/974,913

(22) Filed: Oct. 12, 2001

(65) Prior Publication Data

US 2002/0045195 A1 Apr. 18, 2002

Related U.S. Application Data

(62) Division of application No. 09/689,682, filed on Oct. 13, 2000.

(51) Int. Cl.[7] ............................................. G01N 33/53
(52) U.S. Cl. ........................... 435/4; 435/5; 435/187.1; 435/287.7; 435/970; 435/975; 436/514; 436/518; 436/507; 436/530; 436/807; 436/821; 436/810; 422/56; 422/57; 422/58
(58) Field of Search ................................. 436/514, 518, 436/507, 530, 807, 821, 810; 435/287.1, 287.7, 970, 975; 422/56–58

(56) References Cited

U.S. PATENT DOCUMENTS

| | | | | |
|---|---|---|---|---|
| 4,968,604 A | * | 11/1990 | Beatty | ........................ 435/7.92 |
| 5,486,452 A | * | 1/1996 | Gordon et al. | |
| 5,807,752 A | * | 9/1998 | Brizgys et al. | |

* cited by examiner

Primary Examiner—Bao-Thuy L. Nguyen
(74) Attorney, Agent, or Firm—Jonathan Grant; Grant Patent Services

(57) ABSTRACT

This invention discloses a method and composition for detecting the presence of class specific antibodies reactive with analytes such as bacteria, allergens, autoimmune antigens, viral proteins, and carbohydrates by lateral flow techniques. In one embodiment of the invention, a test sample obtained from bodily fluids reacts with a gold labeled antigen. The resulting complex travels across the membrane, and along the lateral flow strip. Red colored lines formed in specific locations along the test strip indicate the presence of class specific antibodies in the test specimen. In another embodiment of the invention, the lateral flow assay serves as an immunochromatographic screening test for the detection of allergen-specific IgE antibodies in human serum. Test sample reacts with gold labeled anti-IgE antibody. The resulting complex travels across the membrane where immobilized allergens capture the allergen specific IgE complex. Colored lines are formed int the test areas to indicate the presence of allergen-specific IgE antibodies.

10 Claims, 2 Drawing Sheets

INCORPORATION OF SELECTIVE BINDING SUBSTANCES IN A SOLID PHASE ASSAY DEVICE

DESCRIPTION

This following application is a divisional of U.S. application Ser. No. 09/689,682, filed Oct. 13, 2000.

BACKGROUND OF THE INVENTION

1. Field of the Invention

The present invention discloses a method and composition for detecting the presence of antibodies in human or animal bodily fluids (blood, serum, plasma, urine, colostrum, milk, tears, or saliva) to analytes such as bacteria, Chlamydiae, Rickettsiae, protozoa, allergens, autoimmune antigens, viral proteins, and carbohydrates by lateral flow techniques.

2. Description of the Prior Art

Over the years, numerous patents have been issued involving immuno-chromatographic devices. The standard features of these devices comprise the following:

a) A plastic or paper housing allowing the viewing of a reaction area on a bibulous (lateral flow) strip;

b) An opening at one end of the housing allowing for the addition of sample (urine, blood, plasma, serum or bacteria in a media base);

c) Bibulous material (the lateral flow strip) having immobilized specific binding members (analytes) capable of reacting with antigens or antibodies.

d) A pad of absorbent bibulous material (the absorbent pad) enclosed at the end opposite the sample well and used to absorb transversely flowing sample, buffers and colloids;

e) A strip of bibulous material used in the sample well end to initially absorb the sample being applied;

f) A strip of bibulous material in contact with the sample well material and the lateral flow strip and containing a dried colored solid phase reagent, the solid phase coated with proteins or haptens.

Two types of chromatographic immunoassays are commonly described. In the one, proteins or small molecule analytes contained in human fluids (urine, blood, plasma, serum, and saliva) are detected. The analytes include hCG, FSH, LH, CKMB, TSH, troponins, myoglobulin, cancer proteins, viral/bacterial proteins, haptens, therapeutic drugs, and drugs of abuse.

In the other chromatographic immunoassay, the analyte being detected is human antibody specifically reactive with agents such as viral/bacterial proteins (HIV, Hepatitis A and C, *H. pylori*, EBV, Rubella, CMV, HSV, Dengue fever, Lyme, Chagas, TB, Toxoplasma, autoimmune antigens, etc.) or allergens (pollens, molds, dust/mites, foods, animal epithelia, etc.). The various analytes are abbreviated VB for simplified use below. When it comes to detecting antibody, three formats are typically used:

1) The colored solid phase [SP] is coated with proteins or lectins [protein A, protein G, lentil lectin, jacalin, concanavilin A, mannan binding protein, wheat germ lectin, peanut lectin and avidchrom] that react with human IgG antibodies. The solid phase may be coated with anti-immunoglobulins that specifically react with IgG, IgM, IgA, or IgE. The bibulous strip would in this case contain the analyte (VB) of interest to which the specific antibody contained in the sample reacts.

2) The colored solid phase contains the analyte (VB) to which the human immunoglobulins react. The bibulous strip would in this case also contain the analyte (VB) of interest to which the specific antibody contained in the sample reacts.

3) The colored solid phase contains the analyte (VB) to which immunoglobulins react. The bibulous strip contains proteins directed against human IgG or total immunoglobulins (protein A, protein G, lectins, lentil lectin, jacalin, concanavilin A, mannan binding protein, wheat germ lectin, peanut lectin and avidchrom or a mix of antibody to immunoglobulin classes IgG, IgA, IgM and IgE).

U.S. Pat. No. 5,459,041 (Blaser et al.) discloses antigenic compositions for use in diagnostic kits and the like for detecting the presence of antibodies specific for *Campylobacter pylori*. Samples of bodily fluids, for instance, may be contacted with immobilized antigen on a solid phase which is then washed and tested for the occurrence of significant levels of antigen/antibody complex. Levels exceeding a predetermined positive threshold are indicative of antibodies to *Campylobacter pylori* in the sample tested. Kits employing the antigenic compositions of the invention preferably include means for detecting the antigen/antibody complex such as materials and reagents for conducting an enzyme-linked immunosorbent assay, Western blot technique, ELISA, liposome-based assay or other known detection tests. The Western blot and ELISA tests used here are for the detection of IgA and IgG antibodies.

U.S. Pat. No. 5,567,594 (Calenoff) discloses a library of isolated and purified antigens specific for a microorganism is a set of individual molecules. The library forms antigen-antibody complexes useful in the context of diagnosing and treating conditions associated with a specific microorganism such as *H. pylori*-induced gastro-duodenal disease. For the antigen-antibody complexes the antibody in question is an immunoglobulin, which is IgE if the antigens are allergens. Antigen-antibody complexes with IgA, IgG and IgM are also useful if the antigen is a bacteria. By this multivariate approach, a specific condition is diagnosed with high sensitivity and specificity by determining whether complexes form between a specific antigen library and a biological sample which contains immunoglobulins from an individual. Such libraries also are useful for immunotherapy. Western blot is used to detect IgE antibodies. The method requires enzyme conjugates and enzyme substrates and two wash steps to detect antibodies.

U.S. Pat. No. 5,420,014 (Cripps et al.) discloses a method for detecting a current infection by *H. pylori* in a mammal. The method comprises contacting a mucous secretion [saliva] from said mammal with an immobilized antigen component from *H. pylori* for a time and under conditions sufficient for an IgG antibody in said mucous secretion specific to a antigen component to form a complex therewith and then subjecting said complex to a detecting means which involves an enzyme conjugate and specific substrate.

U.S. Pat. No. 6,068,985 (Cripps) discloses a method which uses saliva to detect IgG in both the Western Blot and ELISA tests. This detection method requires the use of an enzyme conjugate and enzyme substrate and two wash steps to detect the antibody.

U.S. Pat. No. 5,846,751 (Pronovost et al.) discloses a sensitive and specific antigen preparation for the detection of *Helicobacter pylori* in biological samples. The preparation uses a range of antigens derived from size exclusion chromatography of detergent-solubilized *H. pylori* cells and the purified antigen preparation is coated on the solid phase.

Serological assays such as ELISA, latex agglutination, and rapid EIA assays are used to detect antibodies to H. pylori. The invention also uses a lateral flow device to detect total immunoglobulins to H. pylori. In this case, the H. Pylori antigen is striped on the membrane reaction area and also coated to the colored solid phase. The antibody in the sample reacts first with H. pylori gold coated conjugate, and then travels to the membrane reaction area where it reacts with striped H. pylori.

U.S. Pat. No. 5,200,344 (Blaser et al) uses a purified p28kd protein from H. pylori to detect IgA, IgM and IgG antibody in ELISA and Western Blot. The test requires conjugate and enzyme substrate and two wash steps to detect the antibody.

U.S. Pat. Nos. 6,060,326 and 5,945,294 (Frank et al.) discloses methods to detect canine IgE using a canine Fc epsilon receptor to detect canine IgE antibodies in a biological sample from a canine.

U.S. Pat. No. 5,547,833 (Dorval et al.) discloses a radial flow assay delivery device, and methods of use.

None of these patents teach or disclose a fast and effective lateral flow assay test for the testing of multiple-class specific antibodies. More specifically, no chromatographic immunoassay is able to distinguish between reactive antibody contained in the classes of human antibody (IgG, IgA, IgM, IgD and IgE). All devices to date detect either total immunoglobulins or IgG. The problem of separating reactivities of antibody class lies in the 10 to 15 fold excess of IgG class specific antibodies over IgA, IgM, and IgE class specific antibodies reactive with analyte (VB) in question at various protein sites (epitopes). If the IgG is allowed to react at the same time or same rate as other classes of antibody, the IgG will mask most if not all the analyte (VB) epitopes, thereby decreasing or eliminating the activity of the IgM, IgA, and IgE class antibodies to the analyte (VB).

SUMMARY OF THE INVENTION

The proposed invention allows for antibody class recognition. In one embodiment of the invention, a lateral flow immunoassay device distinguishes at least three classes of antibody. The classes of antibody to be distinguished include IgG, IgA and IgM. A control line reactive with gold particles is also present.

In another embodiment of the invention, the immunoassay test strip is modified to allow detection of the IgE class of antibody to many allergens (VB) coated sequentially on a bibulous strip. Saturated anti-IgE antibodies coated to colored solid [SP] phase particles at high concentration are reacted with a controlled amount of serum to allow for the near complete complexing of elevated levels of human or other animal IgE. This insures that little free IgE is left unreacted. Unreacted IgE would inhibit the reaction with the multiple analytes coated on the bibulous strip. By capturing most of the IgE on the colored solid phase, sufficient IgE specific antibody molecules are available to react with the various allergens (VB) as the reaction front moves transversely down the strip toward the absorbent pad. This allows for the detection of many different IgE allergen specific molecules.

In both embodiments of the inventions, an IgG reacting protein (which can be protein A, protein G, an antibody to IgG or lectins such as lentil lectin, jacalin, concanavilin A, mannan binding protein, wheat germ lectin, peanut lectin and avidchrom) is added to the sample pad in order to complex the IgG contained in the sample such that the molecular weight of the IgG complex is greater than 1.0 million. This large complex travels sufficiently slower than IgA, IgM, and IgE thereby allowing these antibodies to react prior to the IgG. After reacting to the antigen coated colored solid phase, the various reacted complexes are captured on the bibulous strip coated at three sites with antibody to IgM, IgA and IgG or a protein/lectin reactive with IgG (protein A, protein G, lentil lectin, jacalin, concanavilin A, mannan binding protein, wheat germ lectin, peanut lectin and avidchrom). Thus, the class of reactive antibody is distinguished.

In another embodiment of the invention, the colored solid phase contains proteins that react with IgG, allowing for the detection of many different analyte specific antibody molecules of the IgG class. The reagents coated onto the bibulous lateral flow strip include autoimmune antigens, allergens, Chlamidia, Rickettsiae, viruses, and bacteria.

BRIEF DESCRIPTION OF THE DRAWINGS

The invention will be better understood and further objects, characterizing features, details and advantages thereof will appear more clearly as the following description proceeds with reference to the accompanying diagrammatic drawings given by way of non limiting example only illustrating a presently preferred specific embodiment of the invention.

DETAILED DESCRIPTION OF THE INVENTION

Figure 1:
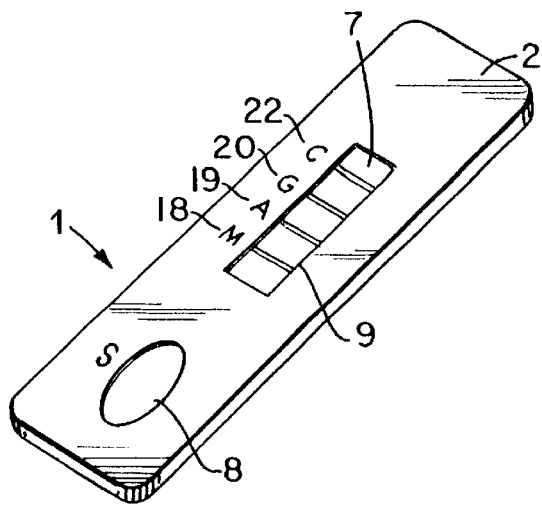
FIG. 1 is a perspective view of one embodiment of the lateral flow immunoassay test.
Figure 2:
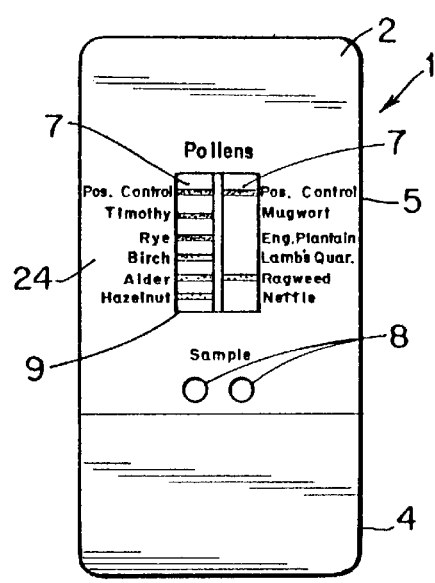
FIG. 2 is a perspective view of another embodiment of the lateral flow immunoassay test.
Figure 3:
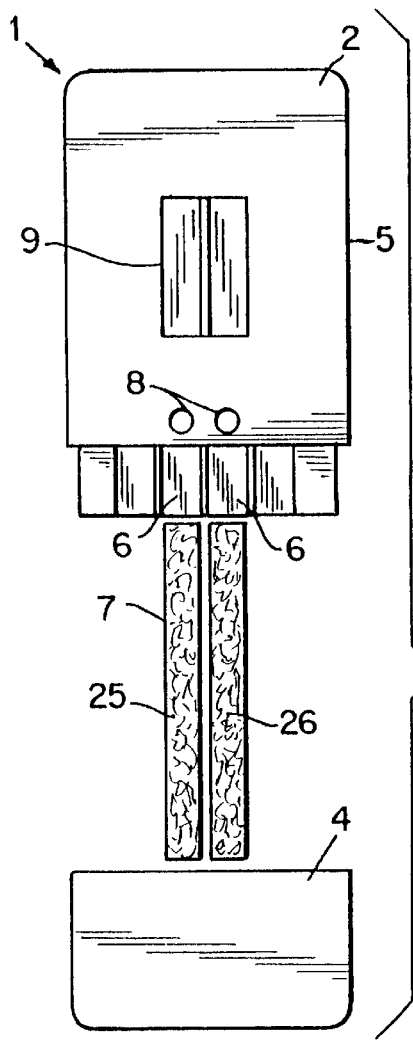
FIG. 3 is an exploded view of the lateral flow immunoassay test.
Figure 4:
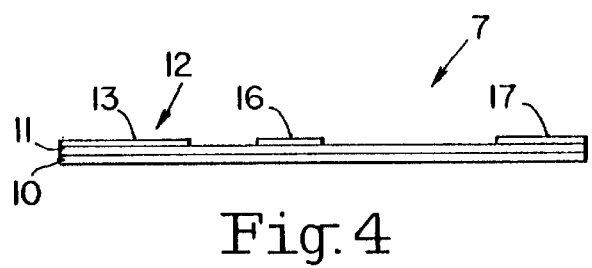
FIG. 4 is a side view of the test strip.
Figure 5:
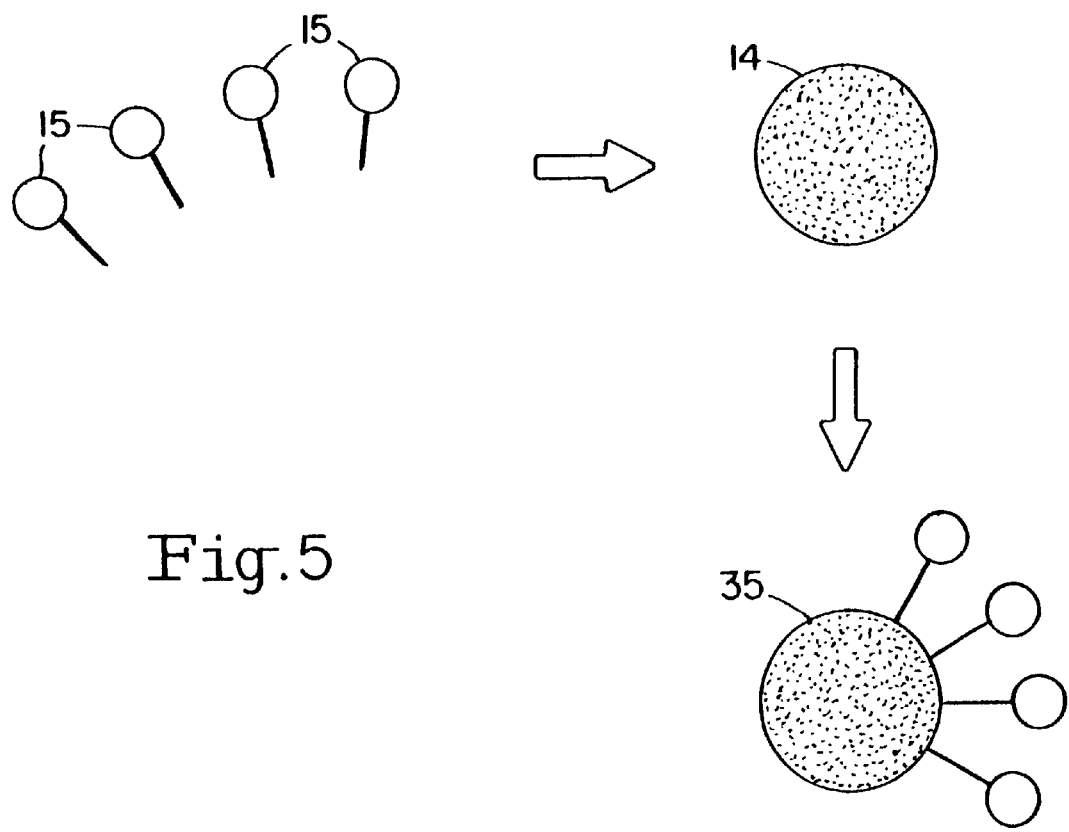
FIG. 5 is a view of the colored particles attached to the antigen.
Figure 6:
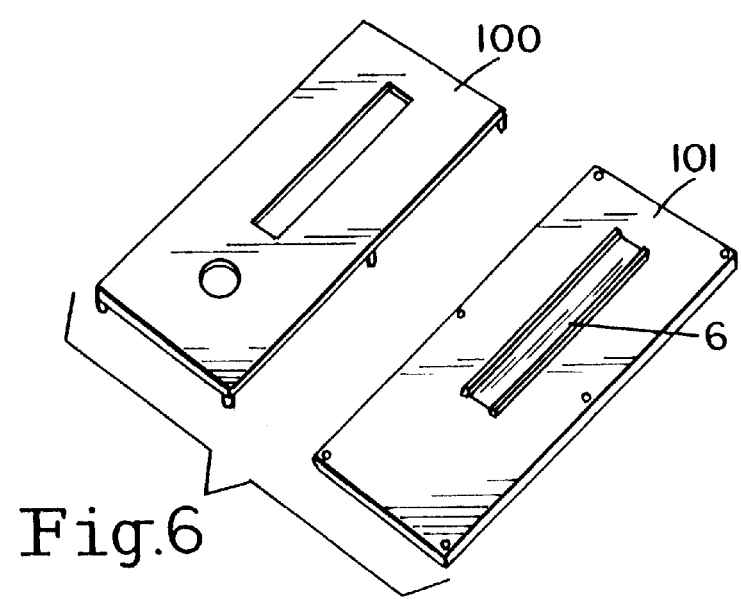
FIG. 6 is an exploded view of another version of the lateral flow immunoassay test.

The immunoassay lateral flow test system 1 comprises a casing 2, preferably plastic, surrounding a test strip 7. On the top surface of the test strip there is a sample opening 8 and a test results opening 9 to show the results of the assay. The casing can take a number of different forms. In FIGS. 3 and 6, the casing has a top section 4 or 100, and a bottom section 5 or 101. Within the top section 4 there is at least one channel 6 into which is fitted a test strip 7. The test strip 7 preferably has a membrane support 10. The membrane support 10 may be comprised of plastic, cardboard, or any other rigid material. On top of the membrane support 10 is a testing layer 11, preferably made out of nitrocellulose. On top of the nitrocellulose or testing layer 11 are the areas to which the appropriate reagents or samples are applied or affixed. The nitrocellulose/testing layer may be affixed to the membrane support 10.

At one end of the test strip 7 is the sample site 12 to which the sample is to be applied. This sample site 12 preferably has a sample pad 13 residing on top of the testing layer, to which the sample is transferred. The sample is preferably a bodily fluid. This fluid may be serum whole blood, plasma, colostrum, milk, saliva, tears, or urine sample from a human or other animal species.

Incorporated in the sample site 12 or sample pad 13, or downstream from the sample site is the labeled antigen, for which the serum is being tested.

The gold particles 14 attached to the antigen or antibody 15 are preferably larger than 20 nm, more preferably in the range of about 20 to 100 nm, and most preferably in the range of 20 to 40 nm. The gold sol labeled antigens/antibodies 35 are dried and deposited on the strip 7.

The metal sol particles to be used in accordance with the present invention may be prepared by coupling the analyte directly to the gold particle. Additionally, the labeled component may be prepared by coupling the analyte to the particle using a biotin/avidin linkage. In this latter regard, the substance may be biotinylated and the metal containing particle coated with an avidin compound. The biotin on the analyte may then be reacted with the avidin compound on the particle to couple the substance and the particle together. In another alternative form of the invention, the labeled component may be prepared by coupling the analyte to a carrier such as bovine serum albumin (BSA), key hole lymphocyananin (KLH), or ovalbumin and using this to bind to the metal particles.

The metal sol particles to be used in accordance with the present invention may be prepared by methodologies which are well known. For instance, the preparation of gold sol particles is disclosed in an article by G. Frens, *Nature*, 241, 20–22 (1973). Additionally, the metal sol particles may be metal or metal compounds or polymer nuclei coated with metals or metal compounds, as described in U.S. Pat No. 4,313,734. Other methods well known in the art may be used to attach the analyte to gold particles. The methods include but are not limited to covalent coupling and hydrophobic bonding. The metal sol particles may be made of platinum, gold, silver, selenium, or copper or any number of metal compounds which exhibit characteristic colors.

Similarly, the analyte does not necessarily have to be attached to a metal sol particle, but may instead be attached to dyed or fluorescent labeled microparticles such as latex, polystyrene, dextran, silica, polycarbonate, methyl-methacrylates and carbon. The metal sol particles, dyed or fluorescent labeled microparticles should be visible to the naked eye or able to be read with an appropriate instrument (spectrophotometer, fluorescent reader, etc. ).

There are a number of ways in which the gold labeled antigens 16 may be deposited on the strip 7.

In an alternative and preferred embodiment, the gold labeled antigens/antibodies are deposited and dried on a rectangular or square absorbent pad 16, the pad preferably about 0.25"×0.25" or less. This absorbent pad 16 is positioned downstream from where the sample is applied on the strip 7.

In yet another embodiment of the invention, the analytes may be attached to microspheres. This has the effect of increasing the number of reactive sites (epitopes) in a given area. Analytes may be attached to these alternate solid phases by various methodologies.

For instance, reactive microspheres (MX-Covaspheres$^R$ of diameter 0.5 micrometers or 0.9 micrometers) purchased from Duke Scientific Corporation, Pal Alto, Calif. 94303, or other suppliers, may be used to covalently attach analytes. The binding is at the amino groups of the protein if covalent methodology is used. In addition, hydrophobic or electrostatic domains in the protein may be used for passive coating. A suspension of the spheres is mixed after sonication with the antigens/antibodies in water or in a phosphate buffer solution, after which they are incubated at room temperature for 10–75 minutes. The mixture is then centrifuged and the pellets containing the antigen/antibody-linked microspheres are suspended in a buffer containing 1–5% wt/volume bovine serum albumin (BSA) for 1 hour at room temperature. The BSA blocks any unreacted surfaces of the microspheres. After one more centrifugation, the spheres are resuspended in buffer (TBS with 5% BSA) and stored at 4 degrees C. before using.

The solid phase particles may comprise any one of known, water dispersable particles, such as, the polystyrene latex particles disclosed in U.S. Pat. No. 3,088,875. Such solid phase materials simply consist of suspensions of small, water-insoluble particles to which antigens/antibodies are able to bind. Suitable solid phase particles are also disclosed, for example, in U.S. Pat. Nos. 4,184,849; 4,486,530; and 4,636,479.

In another embodiment of the invention, the analytes may be attached to fluorescent microspheres or fluorescent microparticles. Said fluorescent micropaticles may be purchased from Duke Scientific, Palo Alta, Calif. 94303 and are listed as Green, Red, or Blue fluorescent 0.4 micron microspheres (Product Bulletin 93). They are also available from Molecular Probes, Eugene, Oreg. 97402 and are listed as FluoroSpheres; Blue, Yellow-Green, Nile Red, Orange, Red, Crimson, Dark Red and Far Red in micron sizes from 0.03 to 5.0. Other manufactures also supply fluorescent microspheres. Characteristically, fluorescent microspheres incorporate fluorescent dyes in the solid outer matrix or in the internal volume of the microsphere. The fluorescent spheres are typically detected by a fluorescent reader that excites molecules at one wavelength and detects the emission of fluorescent waves at another wavelength. For example, Molecular Probes Nile Red particles excite at 526 nm at emit at 574 nm, the Far Red excites at 680 nm and emits at 720 nm and the Blue excites at 365 nm and emits at 430 nm. In a lateral flow format, detection of fluorescent microparticles requires the use of a reflectance reader with an appropriate excitation source (HeNe, Argon, tungsten or diode laser) and an appropriate emission filter for detection. Use of diode lasers allows for use of detection systems that use low cost lasers with detection above 600 nm. Most background fluorescence is from molecules that emit fluorescence below 550 nm.

Fluorescent microspheres contain surface functional groups such as carboxylate, sulfate and aldehyde groups, making them suitable for covalent coupling of proteins and other amine containing biomolecules. In addition, sulfate, carboxyl and amidine microspheres are hydrophobic particles that will passively absorb almost any protein or lectin. Coating is thus similar as for non fluorescent microspheres (Mx-Covaspheres or other latex microparticles). A suspension of the fluorescent spheres is mixed after sonication with the antigens/antibody in water or in a phosphate buffered solution, after which they are incubated at room temperature for 10–75 minutes. EDAC (soluble carbodiimide), succinimidyl esters and isothiocyanates as well as other crosslinking agents may be used for covalent coupling of proteins and lectins to the microspheres. After the protein has attached to the surface of the miroparticles, the mixture is centrifuged and the pellets containing the antigen or antibody linked to the fluorescent microparticles are suspended in a buffer containing 1–5% bovine serum albumin for one hour. After one more centrifugation, the spheres are resuspended in buffer (TBS with 5% BSA or other appropriate buffers) and stored at 4 degrees C. before use.

The solid phase particles useful in connection with the invention may comprise, for example, particles of latex or of other support materials such as silica, agarose, glass, polyacrylamides, polymethyl methacrylates, carboxylate modified latex and Sepharose. The particles will vary in size from about 0.2 microns to about 10 microns. In particular, useful commercially available materials include 0.99 micron carboxylate modified latex, cyanogen bromide activated Sepharose beads (Sigma), fused silica particles (Ciba Corning, lot #6), isothiocyanate glass (Sigma), Reactogel 25DF (Pierce) and Polybead—carboxylate monodisperse microspheres. In accordance with the invention, such particles may be coated with a layer of antigens coupled thereto in a manner known per se in the art to present the solid phase component.

In the preferred embodiment, the sample contains antibodies which will react with the gold labeled antigen, forming an antigen-antibody complex. The gold-antigen antibody complex begins to migrate along the test strip.

Further down the length of the test strip are four binding sites. The first binding site 18 is preferably to bind IgM. The second binding site 19 is preferably a site to bind IgA. The third binding site 20 is for the binding of IgG and the fourth binding site 22 is for a control. More specifically, each binding site is in the form of a striped line along the width of the test strip opening 9. At the site of each binding site, there are anti-Ig immunoglobulins. For example, class specific antibodies are laid down on the test strip. For example, a goat anti-human IgM antibody is laid down at the first binding site 18, goat anti-human IgA antibody is laid down at the second site 19 and goat anti-human IgG antibody is laid down at the third binding site 20. At the control site there is immobilized a protein or substance containing sulfur residues that readily react with any colloidal gold compound. It can also be an antibody reactive with the proteins coated on the gold or microparticles surface. Since the gold or microparticles conjugate is always in excess of sample reactive antibodies, sufficient conjugate is available to react with the control line. The antibodies reactive with IgM, IgA and IgG can be from affinity purification of immune sera from goats, rabbits, donkeys, sheep, chickens or other animals. It may also be monoclonal antibodies directed against IgM, IgA and IgG. The antibodies used are specific for the heavy chain portion of the IgM, IgA and IgG antibodies. Substances reactive with IgG (protein A, protein G, lentil lectin, jacalin, concanavilin A, mannan binding protein, wheat germ lectin, peanut lectin and avidchrom) may be substituted for the antibody to IgG or combined with said antibody.

After the sample has been placed at the sample opening 8, the sample migrates to the site of the gold sol labeled analytes pad 16. Analytes specific for the gold sol conjugate will attach and bind, thus forming gold sol labeled complexes. The gold sol complex continues to migrate along the length of the lateral flow strip. Reactive complexes are specifically captured by analyte (VB) coated on the test strip 7. Migration continues and complexes are captured on the control line of the test strip 7. Excess fluid is wicked into the absorbent pad 17.

The problem of separating reactivities of antibody classes lies in the 10 to 15 fold excess of IgG over IgA and IgM specific antibody reactivity with analyte reaction sites. If the IgG is allowed to react at the same time or rate as other classes of antibody, the IgG will mask most if not all the analyte epitopes, thereby decreasing or eliminating the activity of the IgM and IgA class antibodies to the analyte.

To solve this problem, an IgG reacting substance (which can be, among others, protein A, protein G, an antibody to IgG, lentil lectin, jacalin, concanavilin A, mannan binding protein, wheat germ lectin, peanut lectin and avidchrom) is added to the sample pad in order to complex the IgG such that the molecular weight of the complex is greater than 1 million. This large complex travels sufficiently slower than IgA, IgM, and IgE, thereby allowing these antibodies to react prior to the IgG. After reacting with the colored solid phase, the various reacted complexes are captured specifically at three sites by the antibodies to IgM, IgA, and IgG, or a substance reactive with IgG (protein A, protein G, lentil lectin, jacalin, concanavilin A, mannan binding protein, wheat germ lectin, peanut lectin and avidchrom).

For example, to determine whether a person has been exposed to *Helicobacter pylori*, or to determine if there has been successful treatment of the disease, a serum sample is tested to determine whether it contains antibodies to *H. pylori*. Assuming the use of gold labels, if lines appear at the binding sites for IgG and weakly for IgM, then there is only a chronic condition present. If however, lines appear at the binding sites for IgM and IgA, with or without IgG, then an active or recent colonizing infection is occurring. The detection of IgA when combined with a low serum pepsinogen level is associated with an increased risk of gastric cancer.

This test can detect the presence of class specific antibodies reactive with any bacteria, virus, fungus, irritant, or protein. Some, but not all of the analytes which can be detected using this method include Streptococcus Group A, Streptococcus Group B, Mycobacterium, Mycobacterium tuberculosis, Mycoplasma, Chlamydiae, Rickettsiae, Herpes virus, CMV, Hepatitis A, Hepatitis C, Hepatitis B, Influenza, HIV I, HIV II, HTLV I & II, Chagus, Toxoplasma, Helminh, Nematodes, autoimmune antigens, antibodies to heat shock proteins, transplantation analytes, histocompatability analytes, and combinations thereof.

In another embodiment of the invention, this lateral flow assay can be used for the visual detection of allergen specific IgE antibodies in human or animal serum. In this assay the test serum reacts with a colorimetric (preferably gold) labeled anti-IgE antibody contained in the colorimetric (preferably dried) gold pad. 16. The resulting complex travels along the test strip to the line stripped allergen site 24. At the allergen site, there are a plurality of immobilized allergens 24. Indeed, the immunoassay can easily test for one or more different allergens, preferably by one strip 25, two strips (25 and 26) or multiple strips next to each other. Each strip can contain one or more specific allergen lines. The common allergens which may be tested include but are not limited to pollens (Timothy, cultivated rye, birch, alder, hazelnut, mugwort, English plantain, ragweed, nettle, etc.), dust allergens (*D. farinae, D. pteronyssinus*, house dust), molds (*Alternaria tenuis, Aspergillus fum.*, Cladosporium, Penicillium not), animal epithelium (Cat epithelium, dog dander, horse dander, goose feathers) foods (dairy, cereals, nuts, seafoods, legumes and mixes thereof), inhalant mixes (pollen I (grasses), pollen II (weed/trees), animal mix, dust mix, mold mix) and combinations thereof. The allergens are immobilized on the test strip by the use of solubilizing agents such as sugars and alcohols (sucrose, mannose, fructose, ethylene glycol, ethanol, methanol, glycerin, dextrans). The use of sugars and alcohols unfolds the allergen protein tertiary structure such that more hydrophobic domains are exposed allowing greater binding to the membrane. In addition, protein to protein aggregation is reduced through solubilization allowing individual protein molecules to bind to the nitrocellulose or nylon membrane.

Assuming there is a reaction between the complexes of gold labeled anti IgE antibody and the sample containing IgE antibody and the allergens, a red line will appear at the site of the allergen when there is a positive response. The assay validity is demonstrated by the appearance of a red colored line in the positive control region of the membrane. The positive control is a protein or substance containing sulfur residues that readily react with any colloidal gold compound. It can also be an antibody reactive with the proteins coated on the gold or microparticles surface. Since the gold or microparticles conjugate is in excess, sufficient conjugate is available to react with the control line.

Many modifications and variations of the present invention are possible in light of the above teachings. It is, therefore, to be understood within the scope of the appended claims the invention may be protected otherwise than as specifically described.

What we claim is:

1. A lateral flow immunoassay device for detecting antibodies to a specific analyte, said device comprising:
    a test strip for detecting IgG, IgA and IgM in a sample, said test strip comprising:
        i) a sample site for applying said sample, said sample site comprising:
            a) a sample pad to which said sample is applied; and
            b) an IgG reacting substance present at said sample site, said substance binds to any IgG present in said sample thereby slowing down the migration of said IgG and allowing other antibodies in said sample to migrate and react at sites downstream from said sample pad prior to the migration of said IgG;
        ii) a colorimetric labeling site positioned downstream from said sample site, said colorimetric labeling site comprising colorimetric labeled binding partners for said IgG, IgA and IgM; and
        iii) at least four reaction sites positioned downstream from said colorimetric labeling site, said reaction sites comprising immobilized binding partners for said IgG, IgA, and IgM, and a control reaction site;
    wherein complexes comprising colorimetric labeled binding partner-sample antibody-immobilized binding partner are formed when said antibodies are present in said sample, and a colored line will appear at each of said reaction sites indicating the present of said complexes.

2. The lateral flow immumoassay device of claim 1, wherein said colorimetric label is selected from the group consisting of a metal sol particle, a dyed labeled microparticle, a fluorescent labeled microparticle, and combinations thereof.

3. The lateral flow immunoassay device of claim 2, wherein said metal sol particle is selected from the group consisting of platinum, gold, silver, selenium, and copper.

4. The lateral flow immtmoassay device of claim 1, wherein said analyte is selected from the group consisting of antigens, antibodies, bacteria, virsuses, protozoa, parasites, autoimmune antigens, heat shock proteins, transplantation antigens, histocompatibility antigens, and combinations thereof.

5. The lateral flow immunoassay device of claim 4, wherein said analyte is selected from the group consisting of *H pylori*, Streptococcus Group A, Streptococcus Group B, Mycobacterium tuberculosis, Mycoplasma, Chlamydiae, Rickettsiae, Herpes virus, CMV, Hepatitis A, Hepatitis C, Hepatitis B, Influenza, HIV 1, HIV 11, HTLV I & II, Chagas, Toxoplasma, transplantation antigens, Helminths, Nematodes, autoimmune antigens, heat shock proteins, histocompatability antigens, and combinations thereof.

6. The lateral flow immunoassay device of claim 1, wherein said control site contains an immobilized substance for binding excess labeled binding partner.

7. The lateral flow immunoassay device of claim 1, wherein said immobilized binding partner are affinity purification of immune sera selected from the group consisting of goats, rabbits, donkeys, sheep, chickens, and other animals.

8. The lateral flow immunoassay device of claim 1, wherein said immobilized binding partners are monoclonal antibodies.

9. The lateral flow immunoassay device of claim 1, wherein said IgG reacting substances are selected from the group consisting of protein A, protein C, lentil lectin, jacalin, concanavilin A, anti-IgG, mannan binding protein, wheat germ lectin, peanut lectin, avidcrhom, and combinations thereof.

10. The lateral flow immunoassay device of claim 1, wherein a complex between the IgG reacting substance and the IgG has a molecular weight greater than 1 million.

\* \* \* \* \*